US00PP26880P3

(12) United States Plant Patent
Fretwell

(10) Patent No.: US PP26,880 P3
(45) Date of Patent: Jun. 28, 2016

(54) ***CLEMATIS* PLANT NAMED 'BFCCSAR'**

(50) Latin Name: *Clematis lanuginosa*
Varietal Denomination: BFCCSAR

(71) Applicant: Barry Fretwell, Exeter (GB)

(72) Inventor: Barry Fretwell, Exeter (GB)

( * ) Notice: Subject to any disclaimer, the term of this patent is extended or adjusted under 35 U.S.C. 154(b) by 158 days.

(21) Appl. No.: 13/999,898

(22) Filed: Mar. 31, 2014

(65) Prior Publication Data

US 2015/0282406 P1 Oct. 1, 2015

(51) Int. Cl.
*A01H 5/02* (2006.01)

(52) U.S. Cl.
USPC ..... Plt./228

(58) Field of Classification Search
USPC ..... Plt./228
See application file for complete search history.

(56) References Cited

PUBLICATIONS

PLUTO Plant Variety Database Jul. 22, 2015 p. 1.*

* cited by examiner

*Primary Examiner* — Annette Para
(74) *Attorney, Agent, or Firm* — Cassandra Bright

(57) ABSTRACT

A new and distinct *Clematis* hybrid named 'BFCCSAR' is disclosed, characterized by a distinctive deep cobalt blue flowers with a thin red-purple center streak. Plants have a dense, shrubby plant form and are well suited for container plantings. Semi-double flowers in Spring(May/June), single flowers August/September. The new cultivar is a *Clematis* typically suited for ornamental container and landscape use.

2 Drawing Sheets

Latin name of the genus and species: *Clematis lanuginosa*.
Variety denomination: 'BFCCSAR'.

BACKGROUND OF THE INVENTION

The new cultivar is the result of chance discovery in Hoganas Sweden. The inventor is Barry Fretwell. The new variety was discovered as the result of a breeding program conducted in South Exeter, Great Britain. The seed parent is an unpatented, proprietary *Clematis lanuginosa* seedling referred to as 'P57', the pollen parent is the unpatented variety *Clematis lanuginosa* 'Mrs. N Thompson'. The cross was made Jun. 12, 2000, and the selection of the new variety was made in June 2002.

After selecting and isolating the new cultivar, asexual reproduction of the new cultivar 'BFCCSAR' was first performed in the South Exeter, Great Britain at a nursery by vegetative cuttings in 2005. 'BFCCSAR' has since produced multiple generations, and has shown that the unique features of this cultivar are stable and reproduced true to type.

SUMMARY OF THE INVENTION

The cultivar 'BFCCSAR' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BFCCSAR.' These characteristics in combination distinguish 'BFCCSAR' as a new and distinct *Clematis* cultivar:

1. Deep cobalt blue flowers, with a thin red-purple center streak.
2. White to Greyed-Purple stamens 3. Semi-double flowers in Spring(May/June), single flowers August/September.
4. Dense, bushy plant habit.
5. Suitability for container culture.

PARENTAL COMPARISON

Plants of the new cultivar 'BFCCSAR' are similar to the seed parent variety in most horticultural characteristics. However, the new variety differs from the seed parent in the following:

1. Different colored flowers.
2. Different flower type.

Plants of the new cultivar differ from the pollen parent in the following:

1. Different colored flowers.
2. Different flower type.
3. Shorter internode length.

COMMERCIAL COMPARISON

Plants of the new cultivar 'BFCCSAR' are similar to the commercial variety *Clematis* hybrid 'Evista' U.S. Plant Pat. No. 10,932 in most horticultural characteristics. However, the new variety differs from 'Evista' in the following:

1. The new variety has slightly smaller flowers.
2. The new variety has a dark blue flower color, with a red-purple central streak, whereas 'Evista' flower color is magenta with a red-purple central bar, due to more violet-blue, rather than lavender coloration.
3. The new variety does not have undulating margins.

The new variety can also be compared to *Clematis* 'Lasurstern', differing in the following characteristics:

1. The new variety has smaller flowers.
2. The new variety has a darker flower color.
3. The new variety is denser and shrubbier than 'Lasurstern'.

BRIEF DESCRIPTION OF THE PHOTOGRAPHS

Figure 1:
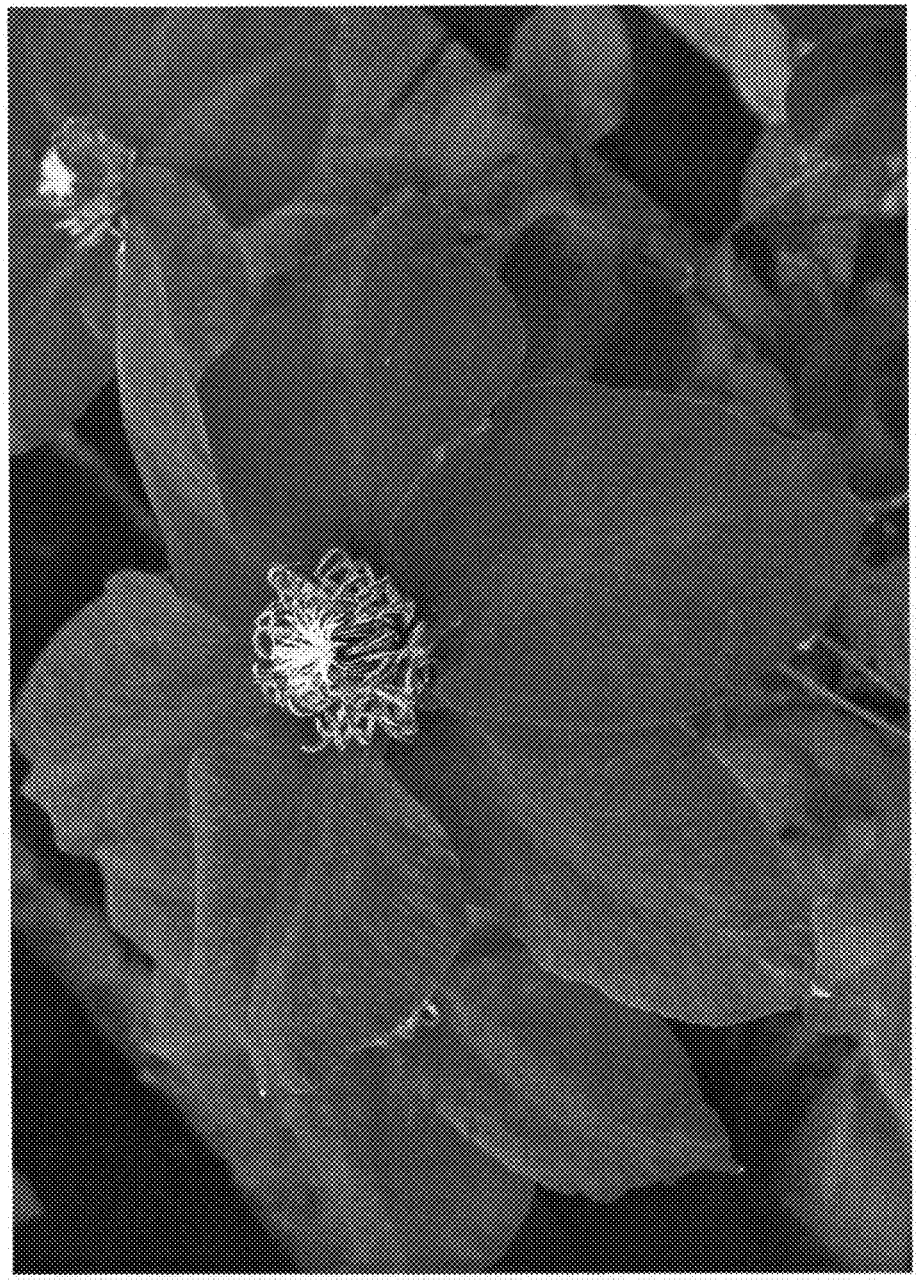

The accompanying photograph in FIG. 1 illustrates in full color a typical mature single flower of 'BFCCSAR' grown outdoors in Germany.

Figure 2:
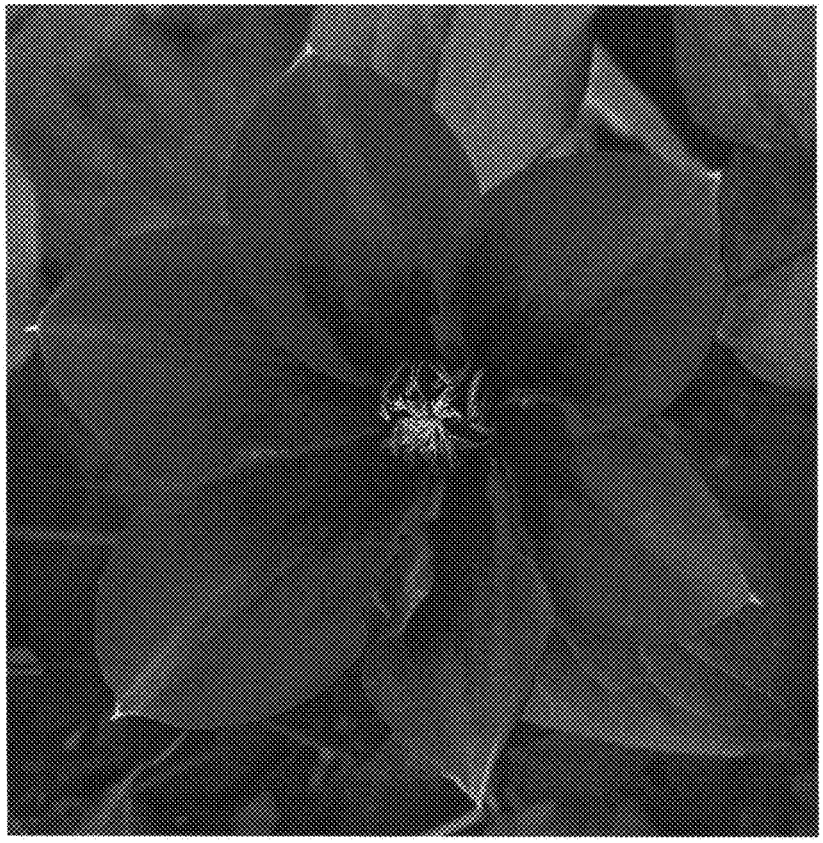

FIG. 2 illustrates in full color a typical immature single flower.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'BFCCSAR' plants grown outdoors in British Columbia, Canada. Measurements were taken in May. The growing temperature ranged from 0° C. to 25° C. at night to 0° C. to 30° C. during the day. No artificial light, photoperiodic treatments or chemical treatments were given to the plants. Plants were pinched twice. Measurements and numerical values represent averages of typical flowering types.

Botanical classification: *Clematis* hybrid 'BFCCSAR'.

Age of the plant described: Approximately 8 months.

Container size of the plant described: Growing in the ground.

PROPAGATION

Typical method: Vegetative cuttings.

Time to initiate rooting: Approximately 20 days at 21° C. or higher.

Time to produce a rooted plantlet: Approximately 20 days at 20° C. or higher.

Root description: Fine, fibrous.

PLANT

Growth habit: Shrubby vine.

Height: Approximately 180 to 250 cm, measured from the soil line of the pot after approximately 8 months.

Plant spread: Approximately 50 to 80 cm.

Growth rate: Rapid during active growing season in Spring.

Branching characteristics: One main stem, easily making side branches from a pinch.

Length of main stem: Approximately 270 cm.

Diameter of main stem: Approximately 0.2 to 0.5 cm.

Main stem color: Near RHS Greyed-Purple N187B.

Main stem texture: Glabrous.

Internode length: Varies from 8 to 15 cm.

Strength: Strong, flexible, semi-woody.

FOLIAGE

Leaf:

*Arrangement*.—Opposite, simple.

*Average length*.—Approximately 6 to 9 cm.

*Average width*.—Approximately 3 to 4.5 cm.

*Shape of blade*.—Oblong.

*Apex*.—Acute.

*Base*.—Cordate.

*Attachment*.—Stalked.

*Margin*.—Entire.

*Texture of both surfaces*.—Glabrous.

*Color*.—Young foliage upper side: Near RHS Green 137A. Young foliage under side: Near RHS Green 137A. Mature foliage upper side: Near RHS Green 137A. Mature foliage under side: Near RHS Green 137A.

*Venation*.—Type: Pinnate. Venation color upper side: Near RHS Green 137A. Venation color under side: Near RHS Green 137A.

Petiole:

*Length*.—Approximately 2.0 to 5.0 cm.

*Diameter*.—Approximately 0.2 cm.

*Texture*.—Smooth.

*Color*.—Near RHS Greyed-Purple 187A.

FLOWER

Bloom period:

*Natural season*.—May through June, and again August through September.

Inflorescence type and habit: Single occurring, axillary. Flowers facing outward and slightly upward. Semi-double flowers in Spring(May/June), single flowers August/September.

Rate of flower opening: Approximately 7 days from bud to fully opened flower.

Flower longevity on plant: Approximately 8 to 15 days, after fully opened. Self-cleaning.

Inflorescence size:

*Diameter*.—Approximately 13 to 15 cm.

*Depth*.—Approximately 4.5 cm.

Single flowers:

*Corolla*.—Tepal arrangement: slightly overlapping single whorl. Quantity: Typically 6 per flower. Size: Length: Approximately 6.5 to 8.0 cm. Width: Approximately 2.5 to 3.8 cm. Margin: Slightly curved under, entire. Apex: Acuminate. Base: Blunt. Texture: Smooth.

*Color*.—Tepals: When opening: Upper surface: Near RHS Blue 99A. Strong center streak near Red-Purple 72B. Lower surface: Near RHS Blue 99C. Faint center streak near Red-Purple 72B. Fully opened: Upper surface: Near RHS Blue 99C. Moderate center streak near Red-Purple 72B. Lower surface: Near RHS Blue 99C. Faint center streak near Red-Purple 72B. Ageing: Upper surface: Near RHS Blue 99C. Weak center streak near Red-Purple 72B. Lower surface: Near RHS Blue 99C.

Semi-double flowers:

*Corolla*.—Tepal arrangement: Overlapping, typically 2 or 3 whorls. Quantity: Typically 24 per flower. Size: Typically quite irregular sizes: Length: Average 5 to 8 cm. Width: Approximately 1.5 to 4.0 cm. Margin: Entire. Apex: Acuminate. Base: Blunt. Texture: Smooth.

*Color*.—Tepals: When opening: Upper surface: Near RHS Blue 99A. Strong center streak near Red-Purple 72B. Lower surface: Near RHS Blue 99C. Faint center streak near Red-Purple 72B. Fully opened: Upper surface: Near RHS Blue 99C. Moderate center streak near Red-Purple 72B. Lower surface: Near RHS Blue 99C. Faint center streak near Red-Purple 72B. Ageing: Upper surface: Near RHS Blue 99C. Moderate center streak near Red-Purple 72B. Lower surface: Near RHS Blue 99C.

Bud:

*Shape*.—Conical.

*Length*.—Approximately 2.7 cm.

*Diameter*.—Approximately 1.8 cm.

*Color*.—Near RHS Violet-Blue 96A.

Peduncles:

*Length*.—Average 14 cm.

*Width*.—Approximately 1.5 cm.

*Angle*.—Average 45° to 75°.

*Strength*.—Flexible.

*Color*.—Near RHS Greyed-Purple N187 C.

Fragrance: None.

REPRODUCTIVE ORGANS

Stamens:

*Number*.—Average 40 per flower.

*Stamen color*.—Near White N155B or Greyed-Purple N187D, flushed Purple N77B.

*Anther length*.—Approximately 1.5 cm.

*Anther color*.—Near RHS Purple N77B.

*Anther shape*.—Oblong.

*Pollen quantity*.—Moderate.

*Pollen color*.—Near White N155C.

Pistil:

*Length*.—Approximately 2 cm.

*Style length*.—Approximately 0.6 to 0.8 cm.

*Stigma*.—Shape: Linear. Color: Near RHS Violet 91D.

OTHER CHARACTERISTICS

Seeds and fruits: Approximately 30 to 60, feathery seeds colored near Grey-Brown 199A.

Disease/pest resistance: Neither resistance nor susceptibility to normal diseases and pests of *Clematis* has been observed.

Temperature tolerance: Tolerates temperatures from approximately −20° C. to 45° C.

What is claimed is:

1. A new and distinct cultivar of *Clematis* hybrid plant named 'BFCCSAR' as herein illustrated and described.

* * * * *